United States Patent [19]

Mathias et al.

[11] Patent Number: 4,985,522
[45] Date of Patent: Jan. 15, 1991

[54] POLYMERS CONTAINING PENDANT UREA GROUPS

[75] Inventors: Lon J. Mathias; David W. Kurz, both of Hattiesburg, Miss.

[73] Assignee: The University of Southern Mississippi, Hattiesburg, Miss.

[21] Appl. No.: 452,362

[22] Filed: Dec. 19, 1989

Related U.S. Application Data

[62] Division of Ser. No. 67,883, Jun. 30, 1987, Pat. No. 4,906,767.

[51] Int. Cl.$^5$ .................... C08F 128/00; C08F 126/00
[52] U.S. Cl. ...................................... 526/288; 526/302
[58] Field of Search ................................. 526/288, 302

[56] References Cited

U.S. PATENT DOCUMENTS 4,514,571 4/1985 Nakai .................... 546/306
4,613,658 9/1986 Mathias .................. 526/312

FOREIGN PATENT DOCUMENTS 1354571 5/1974 United Kingdom .

Primary Examiner—Christopher Henderson
Attorney, Agent, or Firm—Wegner, Cantor, Mueller & Player

[57] ABSTRACT

There is disclosed a family of new vinyl monomers capable of forming polymers by free radical polymerization. The vinyl monomer is of the formula

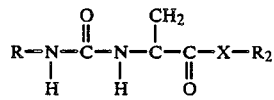

wherein $R_1$ and $R_2$ are substituted or unsubstituted hydrocarbons, X is O, NH or $NR_3$, and $R_3$ is substituted or unsubstituted hydrocarbon.

The intermediates in the synthesis of these monomers are new beta-chloroanaline ureas. The polymers are useful in film and fiber formation and display good toughness. These new vinyl monomers also form a cyclic monomer.

8 Claims, No Drawings

POLYMERS CONTAINING PENDANT UREA GROUPS

This application is a divisional application of U.S. Ser. No. 067,883, filed June 30, 1987, now U.S. Pat. No. 4,906,767.

I. BACKGROUND OF THE INVENTION

Alpha-aminopropenoic acid derivatives having low molecular weight substituents attached to the carbonyl group are known; see for example U.K. Patent Specification 1,354,571 and U.S. Pat. 4,613,658. These compounds are useful as biochemical antibiotic precursors, synthetic nucleic acid mimics, cross-linking agents, monolayers, vesicles, and liquid crystalline solids. The melting point and glass transition point of many of these compounds, however, is low. The low melting point and low glass transition point reduces the utility of these compounds in many applications.

II. SUMMARY OF THE INVENTION

The present invention is directed to new vinyl monomers containing substituted urea pendant groups, the polymers resulting therefrom, and the beta-chloroalanine intermediates of the monomer synthesis. More particularly, the invention is directed to vinyl monomers (alpha-aminopropenoic acid derivatives) of the formula

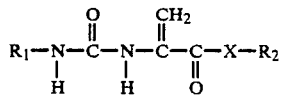

wherein $R_1$ and $R_2$ are substituted or unsubstituted hydrocarbons, X is O, NH, or $NR_3$, and $R_3$ is a substituted or unsubstituted, hydrocarbon. The invention is also directed to the corresponding beta-chloroalanine derivatives which are precursors to the monomers. Polymers can be made from the linear and cyclic monomers using, for example, normal free radical conditions.

The polymers of the present invention have uses such as (i) biocompatible and/or biodegradable encapsulation for controlled drug release, (ii) functional vesicles for antibody or antigen specific diagnostic tests, (iii) in vivo/in vitro studies of the mechanism(s) of endocytosis, (iv) impact modifiers of commercial polymers, i.e., a polymeric plasticizer, and (v) monolayer and Langmuir/Blodgett film-formers which can be subsequently polymerized and used for surface modification and coatings applications. The polymers of the present invention are new thermoplastic or thermoset polymers having a high melting point, high glass transition point, and good toughness. These properties make the polymers resistant to a wider range of temperatures and solvents than the polymers in the aforementioned U.K. Patent 1,354 571 and U.S. Pat. 4,613,658. The polymers can be used for both films and fiber formation.

Due to the presence of the $R_1NH$—group, the compounds of this invention exhibit increased hydrogen bonding over the prior art compounds. This increased hydrogen bonding leads to higher melting points and glass transition points, thereby making the compounds useful for a wider range of applications than the prior art compounds.

DETAILED DESCRIPTION OF THE INVENTION

Alpha-aminopropenoic acid derivatives and their beta-chloroalanine precursors of the present invention are characterized by the presence of an $R_1NH$ group adjacent to the carbonyl moiety. The $R_1$ group can be any substituted or unsubstituted hydrocarbon. Preferably, $R_1$ is selected from the group consisting of substituted and unsubstituted short chain and long chain alkyls, substituted and unsubstituted aryls, and substituted and unsubstituted short chain and long chain aralkyls. In experiments to date, favorable results have been achieved when $R_1$ is selected from the group consisting of $C_1$–$C_{20}$ alkyls, $C_1$–$C_{20}$ aralkyls, $C_1$–$C_{20}$ aralkylsulfonyls, and nitroaryls. Representative $R_1$ groups are methyl, ethyl, propyl, isopropyl, butyl, tert-butyl, cyclohexyl, octadecyl, diisohexyl, phenyl, o-tolyl, m-tolyl, p-tolyl, p-toluenesulfonyl, 4-nitrophenyl, R-(+)-methylbenzyl, and S-(−)-methylbenzyl and isomers thereof.

The $R_2$ group can be any substituted or unsubstituted hydrocarbon. Representative $R_2$ groups are methyl and short chain alkyls. The X group can be O, NH or $NR_3$. $R_3$ can be any substituted or unsubstituted hydrocarbon.

One method for the production of the alpha-aminopropenoic acid derivatives of the present invention is a multi-step procedure starting from commercially available D,L-serine wherein the serine is treated to form the hydrochloride salt (optionally esterified or converted to amide derivatives) which is reacted with phosphorous pentachloride ($PCl_5$) to form 3-chloroalanine hydrochloride salt. The 3-chloroalanine hydrochloride salt is reacted with an isocyanate ($R_1$—N=C=O) to form a 3-chloroalanine derivative of the formula

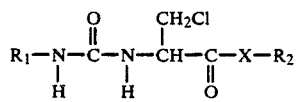

wherein $R_1$, $R_2$ and X are as previously defined. Any isocyanate can be used in this reaction. Given the high reactivity of the isocyanate moiety, all isocyanates will react with 3-chloroalanine via the same reaction mechanism. Thus, $R_1$ can be any substituted or unsubstituted hydrocarbon group. The 3-chloroalanine derivative is isolated and purified by recrystallization, or is reacted with base to form the dehydroalanine derivative comparable to the formula of the alpha-aminopropenoic acid derivatives of the present invention.

The phenyl, o-tolyl, p-tolyl, 4-nitrobenzyl, and methyl dehydroalanine derivatives, and isomers thereof, upon addition of one equivalent of triethylamine base or less, form a cyclic product of the formula

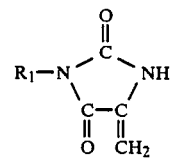

In addition to the methods disclosed supra for the production of alpha-aminopropenoic acid derivatives of the present invention, other synthetic routes are available for the production thereof including the treatment of alanine and cysteine. Other techniques include beta-elimination reactions of (i) O-mesylate or O-tosylate derivatives of serine, (ii) sulfinium or sulfinyl derivatives of cysteine, (iii) cysteine reacted with silver carbonate, and (iv) N-chloro derivatives of alanine. Also available are (v) the Hofmann degradation of diaminopropionyl residues, (vi) the rhenium sulfide catalyzed reaction of anhydrides with methyl-2-azidopropionate, and (vii) direct dehydration of serine residues with triphenylphosphine and diethyl azodicarboxylate or N,N'-disubstituted carbodiimides and cuprous chloride catalyst.

The new monomers of the present invention can be polymerized using free radical techniques and other methods known in the art. The resulting polymer has a structure as follows

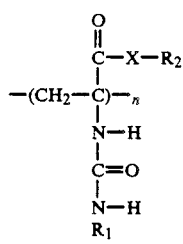

wherein $R_1$, $R_2$ and X are as previously defined and n is an integer greater than or equal to 2. The resulting product has a molecular weight of up to about 15,000,000 and preferably from about 10,000 to about 2,500,000 as estimated by capillary viscometry.

These polymers have been found to be soluble in a variety of organic solvents including acetone, chloroform, 1,4-dioxane, ethyl acetate, methylene chloride, and tetrahydrofuran. The methyl and ethyl derivative polymers are also soluble in water.

The molecular weights of the polymers prepared by the free radical polymerization of the alpha-aminopropenoic acid derivatives of the present invention range from 10,000 to 2,500,000 daltons as estimated by capillary viscometry. Various peroxides and azo initiators can be used in the free radical polymerization. Representative compounds include potassium peroxydisulfate [$K_2S_2O_8$], 2,2'-azobis-(isobutyronitrile) [AIBN], and 2,2'-azobis-(2-amidinopropane) hydrochloride [V-50]. Photoinitiators such as V-50, 2,2-dimethoxy-2-phenyl acetophenone [Irgacure 651], diethoxy acetophenone [DEAP], and benzophenone can also be used.

Bulk or solution polymerization of the monomer usually takes place within four hours at temperatures from room temperature to 100° C. at atmospheric pressure. The methyl, ethyl, R-(+)-methylbenzyl, and S-(−)-methylbenzyl derivatives and isomers thereof spontaneously polymerized at temperatures greater than 60° C. under reduced pressure. Photopolymerization of monomer films takes place after five or less hours of irradiation.

The following examples are representative of the invention.

EXAMPLE 1

Monomer synthesis is accomplished by the methyl esterification, beta-chlorination, and dehydrochlorination of D,L-serine to form dehydroalanine derivatives.

Commercial D,L-serine is reacted with excess HCl saturated methanol at 40° C. for four hours. The solvent is removed under reduced pressure and vacuum oven drying; the D,L-serine methyl ester hydrochloride salt is added in small portions over a period of two hours to a stirred suspension of 10% molar excess phosphorous pentachloride in 2-nitropropane at 10° C. The mixture is kept at 10° C. overnight to complete the reaction. The suspension is filtered and the white crystalline product [3-chloroalanine methyl ester hydrochloride salt] is rinsed with methylene chloride and anhydrous acetone. The 3-chloroalanine methyl ester hydrochloride salt is added to excess ethyl acetate and stirred at 10° C. One molar equivalent of triethylamine base is added and the mixture is stirred for one hour. One molar equivalent of an isocyanate is added portion wise to the stirred suspension over a period of one hour at 10° C. The mixture is allowed to come to room temperature and is stirred overnight to ensure complete reaction. Thin layer chromatography (ethyl acetate solvent) is used to determine when the reaction was complete. The suspension is filtered to remove the triethylamine hydrochloride salt and the filtrate is washed twice with 0.1 N HCl and once with an equal volume of deionized water. Solvent removal under reduced pressure and moderate temperature to remove most of the solvent results in a clear oil product with precipitated the N-(N'-alkylcarbamoyl)-3-chloroalanine methyl ester upon cooling to 10° C. Repeated reprecipitation in ethyl acetate results in a clean product as determined by gas chromatography and $^{13}C$ NMR. The purified 3-chloroalanine product is dissolved in excess ethyl acetate held at 10° C. with vigorous stirring. One equivalent of triethylamine base is added portionwise over a period of one hour and the mixture was brought up to 40° C. for two hours to complete the dehydrohalogenation reaction. The reaction mixture is stored overnight in a refrigerator. Thin layer chromatography (ethyl acetate solvent) is used to determine when the reaction is complete. The mixture is filtered to remove the triethylamine hydrochloride salt and the filtrate is washed twice with 0.1 N HCl and once with an equal volume of deionized water. Solvent removal under reduced pressure and moderate temperature results in a clear oil product which is the N-(N'-alkylcarbamoyl)-dehydroalanine methyl ester. This method affords a clean product which can be easily purified by repeated cold crystallizations from ethyl acetate.

Alternatively, the intermediate beta-chloroalanine urea is not isolated and purified, but is treated directly in the crude reaction mixture with one additional equivalent of triethylamine to give the N-(N'alkylcarbamoyl)-dehydroalanine methyl ester. Purification is then the same as above involving extractions and recrystallizations.

Using the method described above, methyl isocyanate [$CH_3N=C=O$] is used to obtain N-(N'-methylcarbamoyl)-dehydroalanine methyl ester as a clear yellow oil which spontaneously polymerizes upon removal of the solvent at 40° C. under vacuum. Alternatively, addition of one mole equivalent of triethylamine base at room temperature before solvent removal causes the dehdyroalanine derivative to form a cyclic derivative by loss of the ester alcohol group after twenty four hours.

EXAMPLE 2

Using the method described in Example 1, ethyl isocyanate [$CH_3CH_2N=C=O$] is used to obtain the crystalline beta-chloroalanine compound and the N-(N'e- thylcarbamoyl)-dehydroalanine methyl ester as a clear yellow oil which spontaneously polymerizes upon removal of the solvent at 40° C. under vacuum.

EXAMPLE 3

Using a method described in Example 1, propyl isocyanate $CH_3(CH_2)_2N=C=O$ ] is used to obtain the crystalline beta-chloroalanine compound and the N-(N'-propylcarbamoyl)-dehydroalanine methyl ester as a clear yellow oil which is purified by crystallization in ethyl acetate at 10° C.

EXAMPLE 4

Using the method described in Example 1, isopropyl isocyanate $[(CH_3)_2CHN=C=O]$ is used to obtain the crystalline beta-chloroalanine compound and N-(N'-isopropylcarbamoyl)-dehydroalanine methyl ester as a clear yellow oil which is purified by crystallization in ethyl acetate at 10° C.

EXAMPLE 5

Using the method described in Example 1, butyl isocyanate $[CH_3(CH_2)_3N=C=O]$ is used to obtain the crystalline beta-chloroalanine compound and N-(N'-butylcarbamoyl)-dehydroalanine methyl ester as a clear yellow oil which is purified by crystallization in ethyl acetate at 10° C.

EXAMPLE 6

Using the method described in Example 1, tert.butyl isocyanate $[(CH_3)_3CN=C=O]$ is used to obtain the crystalline beta-chloroalanine compound and N-(N'-tert-butylcarbamoyl)-dehydroalanine methyl ester as a clear yellow oil which is purified by crystallization in ethyl acetate at 10° C.

EXAMPLE 7

Using the method described Example 1, cyclohexyl isocyanate $(CH_2)_5CHN=C=O]$ is used to obtain the crystalline beta-chloroalanine compound and N-(N'-cyclohexylcarbamoyl)-dehydroalanine methyl ester as a clear yellow oil which is purified by crystallization in ethyl acetate at 10° C.

EXAMPLE 8

Using the method described in Example 1, octadecyl isocyanate $[CH_3(CH_2)_{17}N=C=O]$ is used to obtain the crystalline beta-chloroalanine compound and N-(N'-octadecylcarbamoyl)-dehydroalanine methyl ester as a clear yellow oil which is purified by crystallization in isomeric hexanes at −40° C. Due to the limited solubility of the 3-chloroalanine derivative, the dehydrohalogenation reaction is carried out at 60° C. in tetrahydrofuran with vigorous stirring. This results initially in a slurry which becomes a clear solution as the reaction proceeds.

EXAMPLE 9

Using the method described in Example 1, 1,6-hexanediisocyanate $[O=C=N(CH_2)_6N=C=O]$ is used to obtain 1,6-bis[N-(N'-diisohexylcarbamoyl) dehydroalanine methyl ester]. The insolubility of the 3-chloroalanine derivative requires dehydrohalogenation reaction conditions as in Example 8.

EXAMPLE 10

Using the method described in Example 1, R-(+)-methylbenzyl isocyanate $[C_6H_5\text{-}CHCH_3\text{-}N=C=O]$ is used to obtain the crystalline beta-chloroalanine compound and N-(N'-R-(+)-methylbenzylcarbamoyl)-dehydroalanine methyl ester as a clear yellow oil which spontaneously polymerizes upon removal of the solvent at 40° C. under vacuum.

EXAMPLE 11

Using the method described in Example 1, S-(−)-methylbenzyl isocyanate $[C_6H_5\text{-}CHCH_3\text{-}N=C=O]$ is used to obtain the crystalline beta-chloroalanine compound and N-(N'-S-(−)-methylbenzylcarbamoyl)-dehydroalanine methyl ester as a clear yellow oil which spontaneously polymerizes upon removal of the solvent at 40° C. under vacuum.

EXAMPLE 12

Using the method described in Example 1, p-toluenesulfonyl isocyanate $[CH_3\text{-}C_6H_4\text{-}SO_2\text{-}N=C=O]$ is used to obtain the crystalline beta-chloroalanine compound and N-(N'-p-toluenesulfonylcarbamoyl)-dehydroalanine methyl ester as a clear yellow oil which is purified by crystallization in ethyl acetate at 40° C.

EXAMPLE 13

Using the method described in Example 1, phenyl isocyanate $[C_6H_5\text{-}N=C=O]$ is used to obtain the crystalline beta-chloroalanine compound and N-(N'-phenylcarbamoyl)-dehydroalanine methyl ester as a clear yellow oil which is purified by crystallization in ethyl acetate at 4°  C. The dehydrohalogenation reaction is carried out at 10° C. Upon addition of one mole equivalent of triethylamine base at room temperature, the dehydroalanine derivative formes the cyclic compound. This product is separated by column chromatography and purified by crystallization in ethyl acetate.

EXAMPLE 14

Using the methods described in Examples 1 and 13, o-tolyl isocyanate $[CH_3\text{-}C_6H_5\text{-}N=C=O]$ is used to obtain the crystalline beta-chloroalanine compound, N-( N'-o-tolylcarbamoyl)-dehydroalanine methyl ester and the cyclic derivative which are purified by crystallization in ethyl acetate at 40° C.

EXAMPLE 15

Using the methods described in Examples 1 and 13, m-tolyl isocyanate $[CH_3\text{-}C_6H_5\text{-}N=C=O]$ is used to obtain the crystalline beta-chloroalanine compound, N-(N'-m-tolylcarbamoyl)-dehydroalanine methyl ester and the cyclic derivative which are purified by crystallization in ethyl acetate at 40° C.

EXAMPLE 16

Using the methods described in Examples 1 and 13, p-tolyl isocyanate $[CH_3\text{-}C_6H_5\text{-}N=C=O]$ is used to obtain the crystalline beta-chloroalanine compound, N-(N'-p-tolylcarbamoyl)-dehydroalanine methyl ester and the cyclic derivative which are purified by crystallization in ethyl acetate at 40° C.

EXAMPLE 17

Using the methods described in Examples 1 and 13, 4-nitrophenyl isocyanate $[NO_2\text{-}C_6H_5\text{-}N=C=O]$ is used to obtain the crystalline beta-chloroalanine compound, N-(N'-4-nitrophenylcarbamoyl)-dehydroalanine methyl ester and the cyclic derivative which are purified by crystallization in ethyl acetate at 40° C.

EXAMPLE 18

Free radical polymerizations are performed in benzene using Vazo 67 initiator at 60° C. One gram of monomer is dissolved in benzene containing 100 mg Vazo 67. Dry nitrogen is passed through the mixture contained in a septum capped test tube for five minutes. The polymerization tube is then placed into a constant temperature water bath maintained at 60° C. for at least four hours and up to 24 hours. Solvent removal results in a clear polymer which is dissolved in tetrahydrofuran and reprecipitated into ice cold methanol. The polymer is vacuum oven dried to remove traces of solvent.

Using the method described above, N-(N'-propylcarbamoyl)-dehydroalanine methyl ester is polymerized, giving a polymer with an intrinsic viscosity of 0.20 dL/g.

EXAMPLE 19

Using the method described in example 18, N-(N'-isopropylcarbamoyl)-dehydroalanine methyl ester is polymerized, giving a polymer with an intrinsic viscosity of 0.54 dL/g.

EXAMPLE 20

Using the method described in Example 18, N-(N'-butylcarbamoyl)-dehydroalanine methyl ester is polymerized, giving a polymer with an intrinsic viscosity of 0.54 dL/g.

EXAMPLE 21

Using the method described in Example 18, N-(N'-tert.Butylcarbamoyl)-dehydroalanine methyl ester is polymerized.

EXAMPLE 22

Using the method described in Example 18, N-(N'-cyclohexylcarbamoyl)-dehydroalanine methyl ester is polymerized, giving a polymer with an intrinsic viscosity of 0.10 dL/g.

EXAMPLE 23

Using the method described in Example 18, N-(N'-diisohexylcarbamoyl)-bis-dehydroalanine methyl ester is polymerized. The product is insoluble in organic solvents.

EXAMPLE 24

Using the method described in Example 18, N-(N'-octadecylcarbamoyl)-dehydroalanine methyl ester is polymerized.

EXAMPLE 25

Using the method described in Example 18, N-(N'-phenylcarbamoyl)-dehydroalanine methyl ester is polymerized.

EXAMPLE 26

Using the method described in Example 18, N-(N'-o-tolylcarbamoyl)-dehydroalanine methyl ester is polymerized.

EXAMPLE 27

Using the method described in Example 18, N-(N'--m-tolycarbamoyl)-dehydroalanine methyl ester is polymerized.

EXAMPLE 28

Using the method described in Example 18, N-(N'-p-carbamoyl)-dehydroalanine methyl ester is polymerized.

EXAMPLE 29

Using the method described in Example 18, N-(N'-p-toluenesulfonylcarbamoyl)-dehydroalanine methyl ester is polymerized.

EXAMPLE 30

At 40° C. under reduced pressure, N-(N'-methylcarbamoyl)-dehydroalanine methyl ester spontaneously polymerizes, giving a polymer with an intrinsic viscosity of 0.40 dL/g.

EXAMPLE 31

At 40° C. under reduced pressure, N-(N'-ethylcarbamoyl)-dehydroalanine methyl ester spontaneously polymerizes, giving a polymer with an intrinsic viscosity of 0.22 dL/g.

EXAMPLE 32

At 40° C. under reduced pressure, N-(N'-R-(+)-methylbenzylcarbamoyl)-dehydroalanine methyl ester spontaneously polymerizes.

EXAMPLE 33

At 40° C. under reduced pressure, N-(N'-S-(−)-methylbenzylcarbamoyl)-dehydroalanine methyl ester spontaneously polymerizes.

EXAMPLE 34

The procedure of Example 1 is repeated, with the exception that excess HCl saturated propanol is substituted for the excess HCl saturated methanol. The resultant monomer is N-(N'-methylcarbamoyl)-dehydroalanine propyl ester.

EXAMPLE 35

The procedure of Example 1 is repeated, with the exception that excess HCl saturated hexanol is substituted for the excess HCl saturated methanol. The resultant monomer is N-(N'-methylcarbamoyl)-dehydroalanine hexyl ester.

EXAMPLE 36

The procedure of Example 1 is repeated, with the exception that the amide derivative of D,L-serine, $CH_2OH.CHNH_2.CONH_2$, is substituted for serine. The resultant monomer is N-(N'-methylcarbamoyl)-dehydroalanine methyl amide, $CH_3NHCO.NHCCH_2CONHCH_3$.

EXAMPLE 37

The procedure of Example 1 is repeated, with the exception that the methylamide derivative of D,L-serine, $CH_2OH.CHNH_2.CONHCH_3$ is substituted for serine. The resultant monomer is N-(N'-methylcarbamoyl)-dehydroalanine dimethyl amide, $CH_3NHCO.NHCCH_2CON(CH_3)_2$.

EXAMPLE 38

The procedure of Example 1 is repeated, with the exception that the octylamide derivative of D,L-serine, $CH_2OH.CHNH_2.CONHC_8H_{19}$ is substituted for serine. The resultant monomer is N-(N'-methylcarbamoyl)- dehydroalanine methyloctyl amide, CH₃NHCO.NHCCH₂CONCH₃C₈H₁₉.

What is claimed is:

1. A polymer containing repeat units of the formula

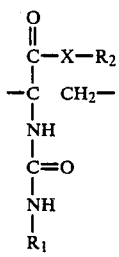

wherein R₁ is selected from the group consisting of C₁–C₂₀ alkyls, C₁–C₂₀ aralkylsulfonyls, arylsulfonyls, unsubstituted aryls, and aryle substituted with methyl and nitro, R₂ is selected from the group consisting of C₁–C₂₀ alkyls, X is O, NH, or NR₃, and R₃ is selected from the group consisting of short chain alkyls.

2. The polymer of chain 1 wherein X is O and R₂ is a short chain alkyl.

3. The polymer of claim 2 wherein R₁ is selected from the group consisting of C₁–C₂₀ alkyls.

4. The polymer of claim 2 wherein R₁ is selected from the group consisting of C₁–C₂₀ aralkyls.

5. The polymer of claim 2 wherein R₁ is selected from the group consisting of C₁–C₂₀ aralkylsulfonyls.

6. The polymer of claim 2 wherein R₁ is selected from the group consisting of nitroaryls.

7. The polymer of claim 2, having a molecular weight between about 10,000 and 2,500,000.

8. The polymer of claim 1 wherein X is O, R₂ is CH₃ and R₁ is selected from the group consisting of methyl, ethyl, propyl, butyl, cyclohexyl, octadecyl, diisohexyl, methylbenzyl, toluenesulfonyl, phenyl, tolyl, nitrobenzyl and isomers thereof.